United States Patent

Maino

Patent Number: 6,155,829
Date of Patent: Dec. 5, 2000

[54] ANCHORING DEVICE FOR ORTHODONTIC CORRECTION TREATMENT INSTRUMENTS

[76] Inventor: Bortolo Giuliano Maino, Via Prati, 2-36100, Vicenza, Italy

[21] Appl. No.: 09/406,145

[22] Filed: Sep. 27, 1999

[30] Foreign Application Priority Data

Sep. 25, 1998 [IT] Italy ................................. VI98A0181

[51] Int. Cl.$^7$ ............................... A61C 8/00; A61C 3/00
[52] U.S. Cl. ............................................... 433/173; 433/7
[58] Field of Search ............................. 433/7, 173, 174, 433/201.1

[56] References Cited

U.S. PATENT DOCUMENTS

| | | | |
|---|---|---|---|
| 5,066,224 | 11/1991 | Bloch et al. | 433/7 |
| 5,769,630 | 6/1998 | Hoffman | 433/7 |
| 5,820,369 | 10/1998 | Kvarnstrom et al. | 433/7 |

*Primary Examiner*—Nicholas D. Lucchesi
*Attorney, Agent, or Firm*—Dykema Gossett PLLC

[57] ABSTRACT

The invention consists of an anchoring device to be applied in the palatal arch to anchor the wires suitable for orthodontic treatment. Said anchoring device consists of: the first screw (1) with a threaded shank (11; 12) topped by a substantially cylindrical collar (13), with non cylindrical head (14) of reduced width as compared to the diameter of said collar; said first screw has a threaded hole (15) coaxial to the axis of said first screw; a substantially cylindrical distance sleeve with two central hollows (62; 63), the first hollow (62) non cylindrical and with a profile suitable to mate with said collar (14) of said first screw. The second hollow (63) has a substantially cylindrical profile suitable to the passage of the shank (71) of a second screw (7). The second screw (7) has a head (73) topping said cylindrical shank and a threaded end part (72), where said head has a threaded hole (74) suitable for receiving said locking screw (10) of the cap (8).

7 Claims, 3 Drawing Sheets

ANCHORING DEVICE FOR ORTHODONTIC CORRECTION TREATMENT INSTRUMENTS

The invention is relative to an anchoring device to be applied in the palatal arch to anchor to it the devices used in orthodontic correction.

The technique of the correction of tooth malformation (also known as orthodontics) makes use of correction instruments consisting of wires, bars and other mechanical elements for traction and/or pressure that exert an action respectively of traction and/or pressure in the required directions on the teeth needing correction. For the sake of simplifying the description the word "wires" will be used hereinafter for wires proper, as well as for bars or other mechanical elements.

Some of the latest known anchoring devices include a fastening element with a threaded end suitable for screwing into the palatal bone and the other end provided with a shaped head to anchor to it one or more orthodontic connecting wires. Said two ends are joined together by means of a substantially cylindrical shank belonging to the only piece forming the fastening element, said shank in substance corresponding to the part that passes through the gum.

The shaped head protruding from the gum and receiving the anchoring wires is also suitable to be covered by a cap provided with a face interspaced by at least two notches suitable to the passage of said wires; this cap consents tightening and locking of said wires by means of a through screw in the hole of the cap head and a lag screw in the head of said fastening element.

When the orthodontic correction treatment is concluded and all anchoring elements connected to the above mentioned fastening element screwed in the palatal bone have been removed, it is necessary to remove also this last element, at least the head of which protrudes from the palatal gum.

This operation requires a further surgical act with possible implanting of bone filling to close up the hole that would remain to permit the re-growth of gum tissue above the place where the device was removed.

Furthermore, said anchoring devices have the threaded end made to screw into the spongy medullar part of the palatal bone, while the shank length is such as to normally perforate the compact cortical part, the periost and the gum in sequence.

In these devices the anchoring stability is limited by the fact that the surface of the shank in contact with the compact cortical part of the bone is too small.

Recently, with the intent of exploiting the surface resting on the cortical bone part, experimental devices have been examined including a long enough plate that will support the anchoring head of the wires and is applied subperiostically, in contact with the cortical bone surface, by means of biocompatible adhesives.

Anchoring stability is in this case assured mainly by the action of said adhesives, which are not yet guaranteed as to stress endurance capacity.

This invention intends to overcome the limitations and inconveniences mentioned above.

In fact, the intention is to create an anchoring device utilizing the well-known and by now widely tested technique of insertion by means of screwing into the spongy part of the bone, though at the same time fully exploiting the more secure anchoring action to the compact cortical part of the bone.

It is also the intention to create an anchoring device that at the end of the orthodontic correction treatment would not require a surgical operation for the removal of the screw inserted into the palatal bone.

These aims are attained by means of an anchoring device to be applied in the palatal arch to anchor wires suitable for orthodontic correction, including a fastening element to be screwed into the palatal bone and a cap blocked to the part of said fastening element that protrudes from the gum covering the bone, said cap having a hollow suitable for housing said protruding part of said fastening element, with a face interspaced by at least two notches suitable for the passage of said orthodontic wires, and having at the top a through hole suitable to lodge the head of a screw blocking the cap on the fastening element, where this device, according to the contents of the first claim, is characterized in that said fastening element includes the following:

a first screw with a threaded shank topped by a substantially cylindrical collar, above which there is a non cylindrical head of reduced width as compared with the diameter of said collar, said first screw having a threaded hole coaxial to the axis of said first screw;

a distance sleeve with substantially cylindrical outer surface, with two central mutually coaxial hollows; the first hollow non-cylindrical and with a profile suitable to mate with said head of said first screw, the second hollow, contiguous to the first, having a substantially cylindrical profile suitable to the passage of the cylindrical shank of a second screw.

a second screw, with a non cylindrical head topping said cylindrical shank and a threaded end part, where said head of said second screw has a threaded hole suitable for receiving said locking screw of the cap.

The above purposes will be more fully illustrated further along in the course of the description of the preferred manner of application of the invention, given by way of indication but without implying any limitation, and represented in the enclosed diagrams, where:

Figure 1:
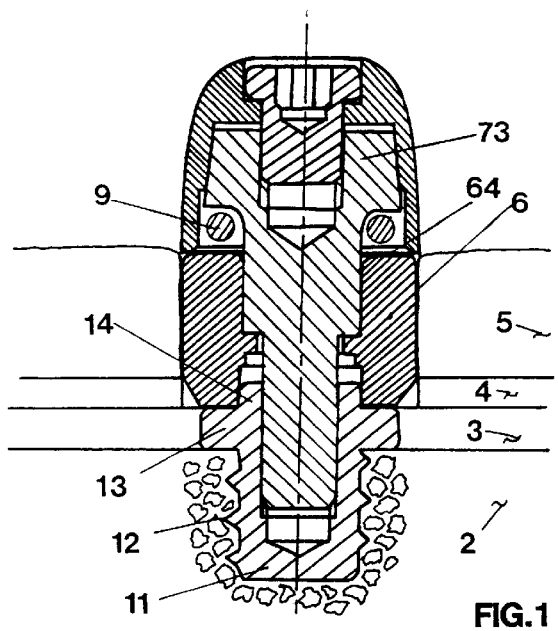
FIG. 1 shows, in axial section, the anchoring device complete with all its components and applied to the bone of the palatal arch.

With reference to FIGS. 1 to 5 the anchoring device of the invention has the first screw 1 with the shank 11 provided with outer threading (12) intended to be screwed into the spongy part 2 of the palatal bone and on the inside connected with the threaded blind hole 15, made to hold the threaded end of the second screw 7.

Said first screw also has the substantially cylindrical collar 13, with a larger diameter than that of the screw shank and depth no greater than the cortical part 3 of said bone.

Said collar is topped by head 14, preferably with a hexagonal profile and in any case not cylindrical, consenting the screwing maneuver of the first screw by means of a suitable instrument, and the lodging of the distance sleeve 6.

Evidence is given to the fact that the first screw 1 is correctly placed with the threaded shank 11 fully imbedded in the medullar part 2 of the bone, while the collar 13 perfectly adheres to the lodging surface created with an end milling cutter in the cortical part 3 of said bone. Head 14 presents its upper surface 141 (FIG. 2) which is substantially at the same level or emerges only slightly from the surface joining periost 4 and gum 5.

Figure 5:
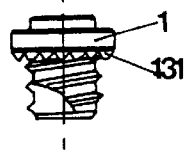
FIG. 5 shows a variation in use of the element of FIGS. 3 and 4.
Figure 3:
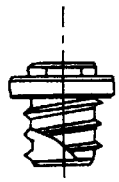
FIG. 3 shows the first screw of the device seen from the front.
Figure 4:
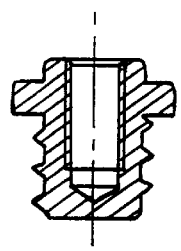
FIG. 4 is an enlarged axial section of the same element as FIG. 3.

A satisfactory variation in execution represented in FIG. 5 has collar 13 with the lower basis surface provided with roughness 131 obtained by means of well-known techniques contributing, by biting into the cortical part of the bone (FIG. 2), to increase resistance of screw I by increasing the surface in direct contact with the bone.

The anchoring device also includes the distance sleeve 6 (FIGS. 1, 2, 6 and 7), with a substantially cylindrical outer surface 61 of a depth at least equal to the thickness of the gum 5 (FIG. 1), and this sleeve presents on its inner surface two main hollows 62 and 63 that are mutually coaxial.

The first hollow 62, non-cylindrical, has a profile such as to consent mating with head 14 of the first screw 1 (FIG. 1) thus preventing its rotation with respect to the screw itself.

The second hollow 63 is contiguous to the first and has a substantially cylindrical profile since it is suitable to receive the cylindrical shank of the screw 7 in its non-threaded middle part 71, when the threaded end 72 of said second screw is fully screwed into hole 15 of the first screw 1 (FIG. 1).

Said second screw 7 presents the head 73, topping cylindrical shank 71, with a preferably truncated-pyramid profile and is provided at the center with a threaded hole 74 intended to lodge screw 10 to block cap 8.

The depth of the non-threaded part 71 of the shank of this second screw is such that when it is fully embedded in the first screw, with distance sleeve 6 between them, it leaves between the upper rim 64 of the distance sleeve and the lower basis surface of the head 731 sufficient space to lodge at least one wire 9 (FIG. 1).

Said wire can be of the type with pre-formed slot to hook on to the shank of the second screw just below its head, or of the straight type passing laterally to the shank.

Figure 11:
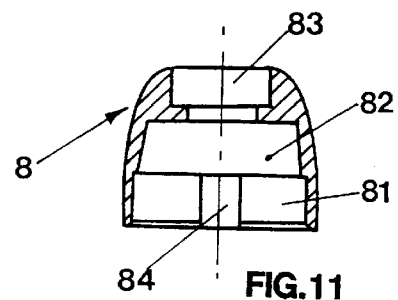
FIG. 11 is an enlarged axial section of the same element of FIG. 10.
Figure 8:
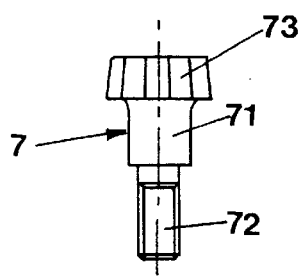
FIG. 8 shows the second screw of the invention device seen from the front.
Figure 9:
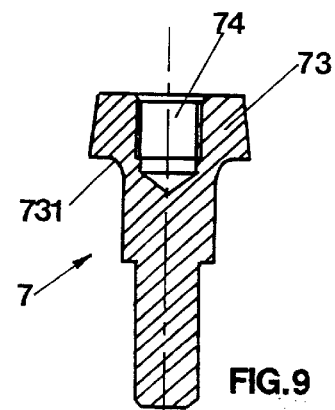
FIG. 9 is the enlarged axial section of the same element of FIG. 8.
Figure 6:
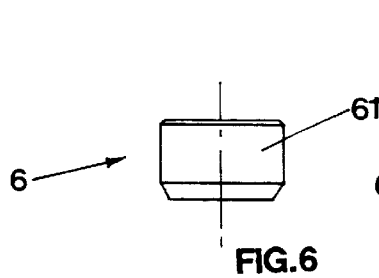
FIG. 6 shows the distance sleeve of the invention device seen from the front.
Figure 7:
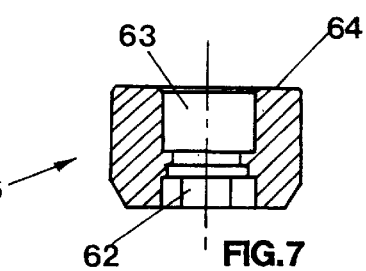
FIG. 7 is the enlarged axial section of the same element of FIG. 6.

The blocking of the wire occurs by means of cap 8 (FIGS. 1, 2, 10, 11) presenting a hollow formed by a first cylindrical part 81 (FIGS. 2, 11) and a second part 82 with a profile suitable to mate with head 73 of the second screw 7 thus preventing rotation of the cap with respect to the head itself.

For this purpose said cap presents at the top a central hole 83 for the passage of screw 10 blocking the cap to head 73 of the second screw.

This maneuver also consents tightening wire 9 between the upper rim 64 of the distance sleeve 6 and the lower surface 731 of the head of the second screw 7 (FIG. 1).

The outlet of wire 9 from the cap face is consented by the presence in the face itself of at least two hollows 84 (FIGS. 2, 10, 11) that are either diametrically opposed or adjacent.

As may be seen in FIG. 1, the wire anchoring device 9 composed of all of its elements ensures secure stability, since it fully exploits the anchoring action particularly in the cortical part 3 of the bone.

Figure 14:
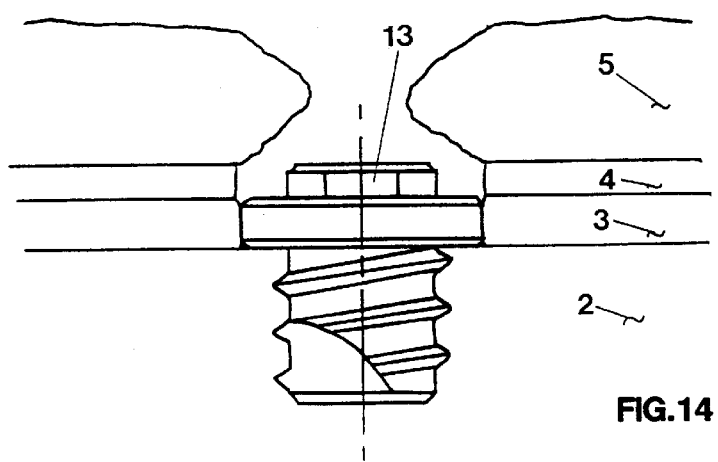
FIG. 14 shows the first screw of the device left in the screw hole at the end of the orthodontic correction treatment.
Figure 15:
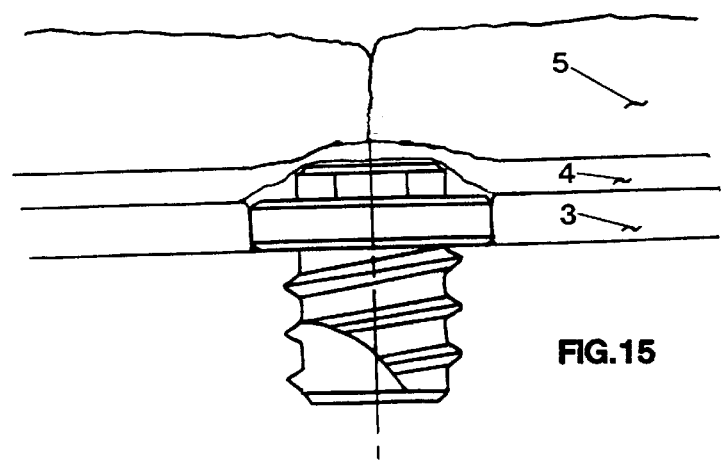
FIG. 15 shows the final covering of said first screw by the healed gum.
Figure 2:
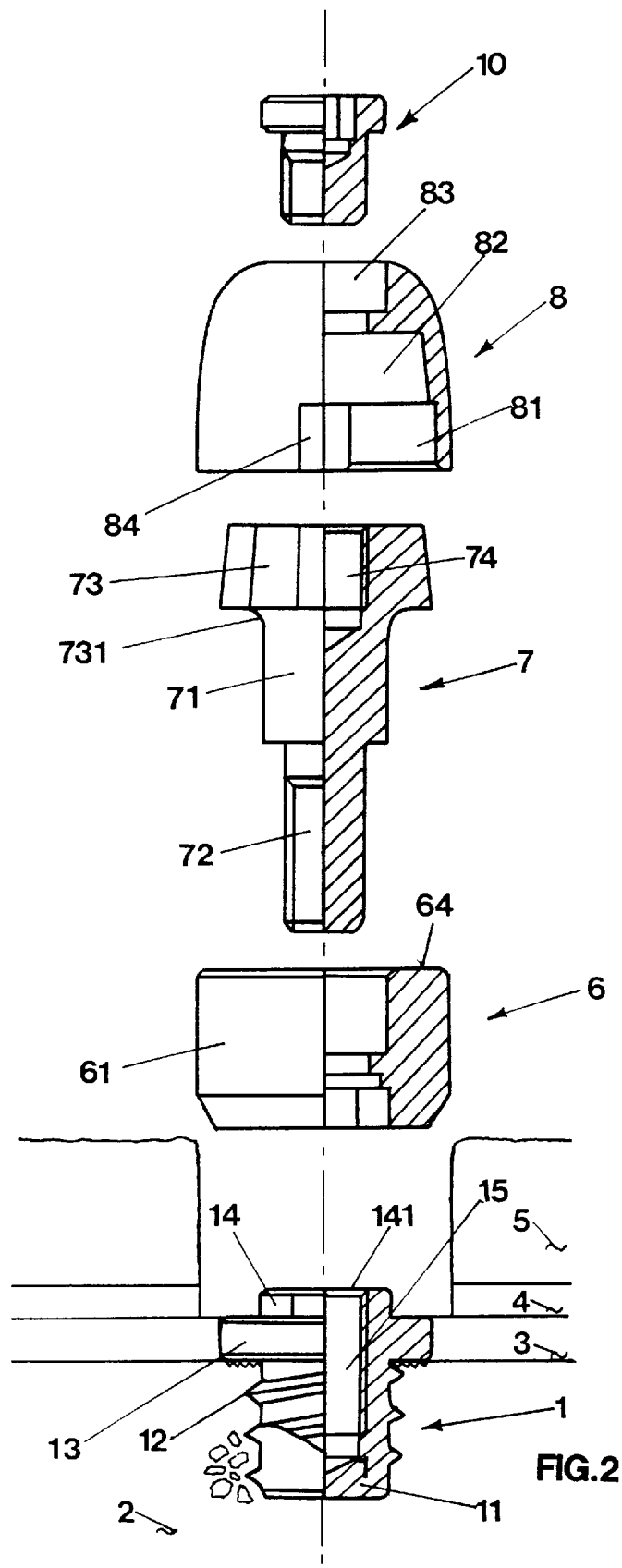
FIG. 2 shows, in an enlarged view, all the partially sectioned elements making up the device itself.
Figure 12:
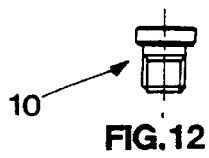
FIG. 12 shows the locking screw of the cap seen from the front.
Figure 13:
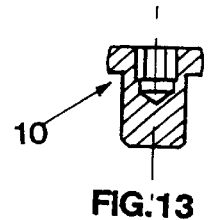
FIG. 13 is an enlarged axial section of the same element of FIG. 12.
Figure 10:
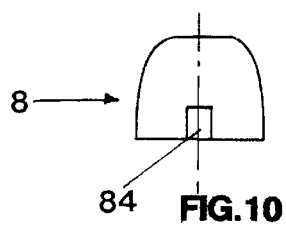
FIG. 10 shows the cap of the invention seen from the front.

When the orthodontic correction treatment is considered concluded, disassembly of the elements external to the gum makes it possible to leave embedded in the bone only the first screw 1 of the device itself (FIG. 14) whose upper head 13 is substantially on the same level or emerges slightly from the periost surface 4.

In this way the gum 5 can grow back and definitively cover the head of the screw itself eliminating the need for a subsequent operation for the removal of the fastening element which is always required with the known devices with possible application of fillings to close the hole left by the screw.

From all the above it is clear that the blocking device of the invention attains all the required purposes. While in a phase of execution the material, usually titanium, the shapes and dimensions of the component elements of the device itself, can vary according to construction requirements and to the different structure of the mouth in which the device is to be applied.

In particular the depth of the distance sleeve 6 can vary to correlate it to the thickness of the gum 5 (FIGS. 1 and 2), as well as the length of the shank 71 of the second screw 7 which must correlate with said depth of the distance sleeve and the diameter of the wires 9.

It is however understood that any possible variations from the example to be realized, as described and illustrated, are to be considered protected by this invention.

What is claimed is:

1. An anchoring device to be applied to the palatal arch to anchor wires suitable for an orthodontic correction treatment comprising a fastening element to be screwed into the plalatal bone and a cap blocked on a part of said fastening element having a protruding extending from the gum covering the bone, said cap having a hollow for engaging said protruding part in spaced relationship forming at least two hollows for the passage of orthodontic wires, and having at the top a through hole suitable to receive the head of a locking screw on the fastening element, wherein said fastening element includes:

a first screw with a threaded shank for engaging the palatal bone and a substantially cylindrical collar atop the first screw and, a non-cylindrical head atop the cylindrical collar having a reduced width as compared to the diameter of said collar, said first screw having a threaded hole coaxial with an axis of said first screw;

a distance sleeve with substantially cylindrical outer surface having two mutually alligned coaxial central hollows, the first hollow being non-cylindrical and with a profile suitable to mate with said head of said first screw; the second hollow, contiguous to the first having a substantially cylindrical profile;

a second screw having a cylindrical shank, a head atop said cylindrical shank and a threaded end part, where said head has a threaded hole for receiving said locking screw of the cap and said cylindrical shank passes through the second hollow of the distance sleeve.

2. The anchoring device according to claim 1, wherein the head of said second screw has a truncated-pyramid profile.

3. The anchoring device according to claim 1, wherein the collar of said first screw has a depth does not exceed the thickness of the cortical part of the bone.

4. The anchoring device according to claim 1, wherein the head of the first screw has a height such that it extends to or above the periost.

5. The anchoring device according to claim 1, wherein the distance sleeve has a depth at least equal to the thickness of the gum.

6. The anchoring device according to claim 1 for securing wires of a selected diameter therein, wherein the second hollow has a selected height and the cylindrical sleeve has a corresponding length which exceeds the length of said second cylindrical hollow by an amount substantially equal to the diameter of said wires.

7. The anchoring device according to claim 1, wherein the collar of said first screw has a lower base formed with roughness to engage the cortical part of the bone.

\* \* \* \* \*